(12) United States Patent
Chiang

(10) Patent No.: US 8,297,105 B2
(45) Date of Patent: Oct. 30, 2012

(54) IMPACT TESTING DEVICE AND IMPACT TESTING METHOD USING THE SAME

(75) Inventor: Tsung-Hsun Chiang, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 211 days.

(21) Appl. No.: 12/873,218

(22) Filed: Aug. 31, 2010

(65) Prior Publication Data
US 2011/0247393 A1    Oct. 13, 2011

(30) Foreign Application Priority Data
Apr. 8, 2010    (TW) ................................ 99110835 A

(51) Int. Cl.
G01N 3/00    (2006.01)
G01N 19/02    (2006.01)
G01M 7/00    (2006.01)
(52) U.S. Cl. .................................... 73/12.06; 73/12.04

(58) Field of Classification Search ................... 73/12.6, 73/12.04
See application file for complete search history.

(56) References Cited

U.S. PATENT DOCUMENTS
7,913,539 B2 *    3/2011    Su ................................ 73/12.06
* cited by examiner Primary Examiner — Lisa Caputo
Assistant Examiner — Jamel Williams
(74) Attorney, Agent, or Firm — Altis Law Group, Inc.

(57) ABSTRACT

An impact testing device for a test subject includes a supporting member, a suspending arm with an end fixed on the supporting member, and the other end of the suspending arm being a free end, and a fixing mechanism fixed on the suspending arm adjacent to the free end of the suspending arm to fix the test subject.

8 Claims, 4 Drawing Sheets

IMPACT TESTING DEVICE AND IMPACT TESTING METHOD USING THE SAME

BACKGROUND

1. Technical Field

The present disclosure relates to device testing and, particularly, to an impact testing device and an impact testing method using the same.

2. Description of the Related Art

A test subject is normally tested before packaging to ensure meeting quality standards. Such testing may involve dropping from a predetermined height, with an oscillating curve of the test subject recorded by a sensor for analyses. However, duration of impact for the test subject is very short (several milliseconds), thus complicating analysis, especially when the size of the test subject is relatively small. During the impact testing, the impact strength for the sudden impact can be increased by raising the height of the impact test device. However, the duration of impact is mostly dictated by the material properties of the cushioning material, and because of material constraints of the cushioning properties, therefore, it is difficult to significantly improve upon the impact duration.

Therefore, there is room for improvement within the art.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views, and both the views are schematic.

DETAILED DESCRIPTION

Figure 1:
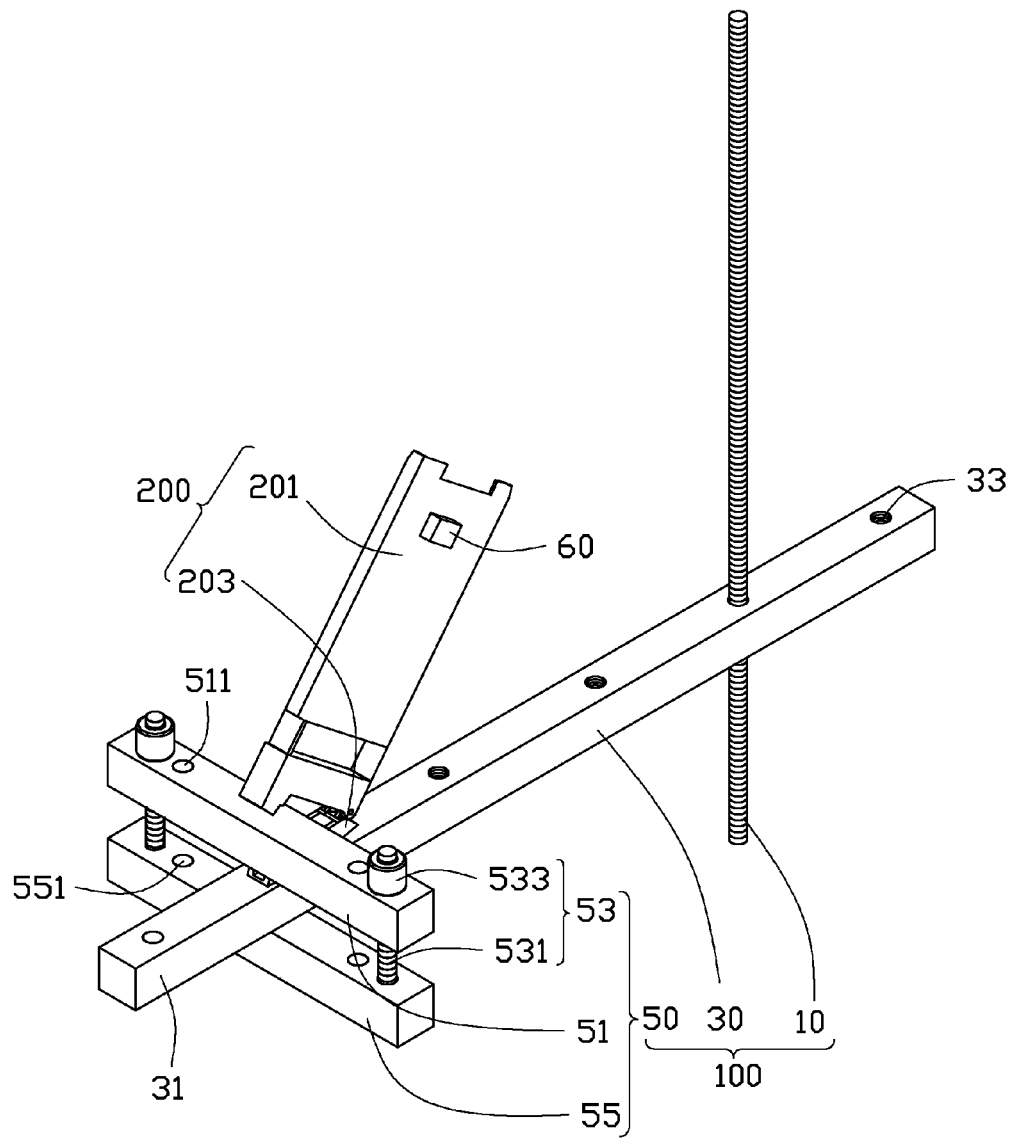
FIG. 1 is an isometric view of an embodiment of an impact testing device, with a test subject.
Figure 2:
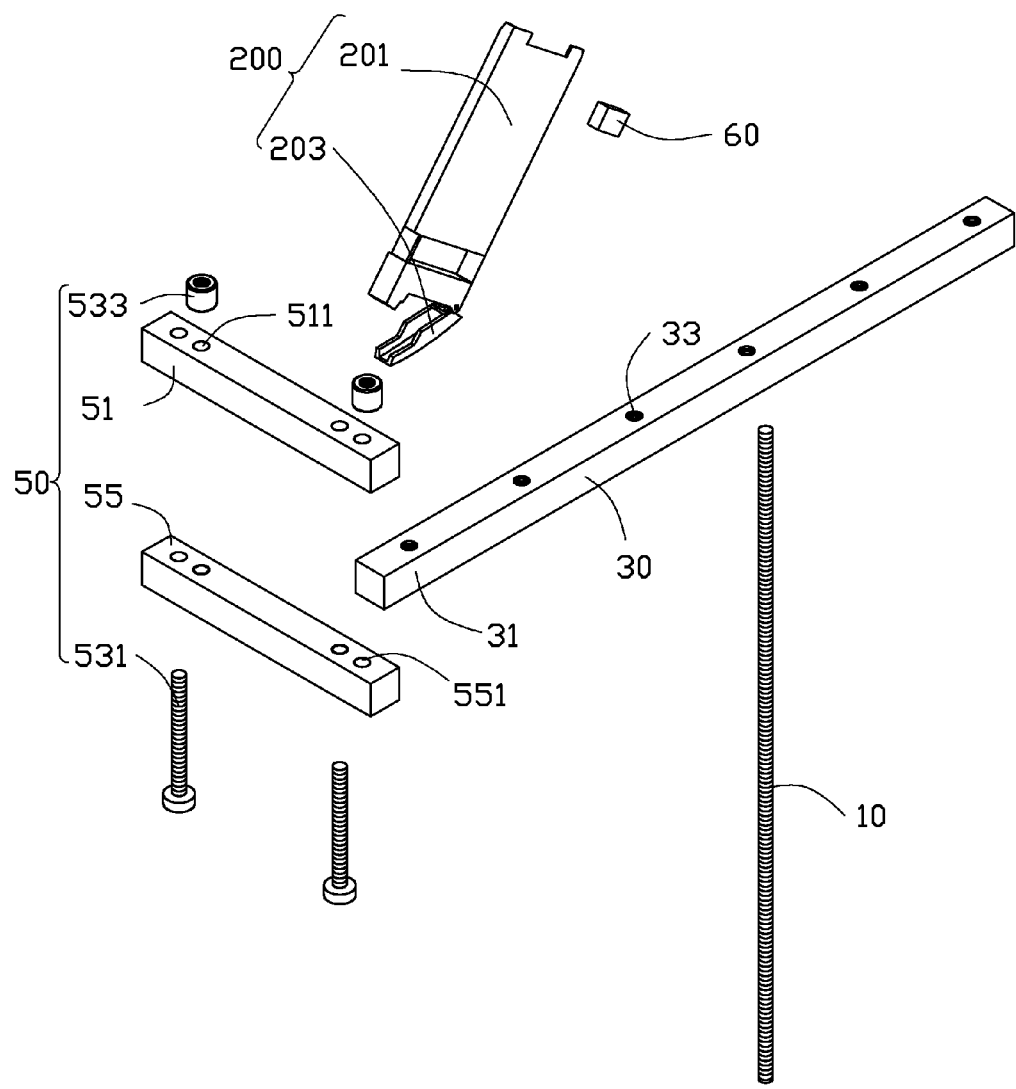
FIG. 2 is an exploded, isometric view of the impact testing device and the test subject shown in FIG. 1.

Referring to FIGS. 1 and 2, an exemplary embodiment of an impact testing device 100 includes a supporting member 10, a suspending arm 30 on the supporting member 10 and a fixing mechanism 50 mounted on the suspending arm 30. In the illustrated embodiment, the supporting member 10 is a threaded rod. A bottom end of the supporting member 10 is fixed on a table (not shown) or on a base. Alternatively, the supporting member 10 may be a base or a seat.

The suspending arm 30 includes a free end 31 and a plurality of receiving portions 33. In the illustrated embodiment, the suspending arm 30 is a post, and the receiving portion 33 is a threaded hole. Alternatively, the receiving portion 33 may be a post or a plate extending from the suspending arm 30, with the supporting member 10 fixed thereto via the receiving portion 33. In addition, the suspending arm 30 can be of a bar structure.

The fixing mechanism 50 includes a holder 51, two adjusting members 53 and a fixing member 55. In the illustrated embodiment, the holder 51 is a bar defining a plurality of connecting holes 511. Each adjusting member 53 includes a threaded rod 531 and a threaded retainer 533 corresponding to the threaded rod 531. The holder 51 and the fixing member 55 are substantially the same in structure. The fixing member 55 defines a plurality of fixing holes 551 corresponding to the connecting holes 511 of the holder 51, respectively. Alternatively, both the fixing member 55 and the holder 51 may be comprised of a plurality of plates or bars, and one, three, four or more adjusting members 53 may be deployed.

In assembly, the supporting member 10 passes through the receiving portion 33 of the suspending arm 30 such that the supporting member 10 adjustably supports the suspending arm 30 by fixing to other mounting structures (not shown). The fixing member 55 is fixed at one side of the suspending arm 30 adjacent to the free end 31 of the suspending arm 30. An end of the threaded rod 531 is threaded in the fixing hole 551 of the fixing member 55, and the other end of the threaded rod 531 passes through the holder 51 and extends out of the holder 51. The threaded retainer 533 is threaded on the end of the threaded rod 531 out of the holder 51 to prevent the holder 51 from detaching from the fixing member 55.

FIG. 2 shows the impact testing device 100 employed for testing a test subject 200. In the illustrated embodiment, the test subject 200 is a frame, which includes a main body 201 and a connecting member 203.

Figure 3:
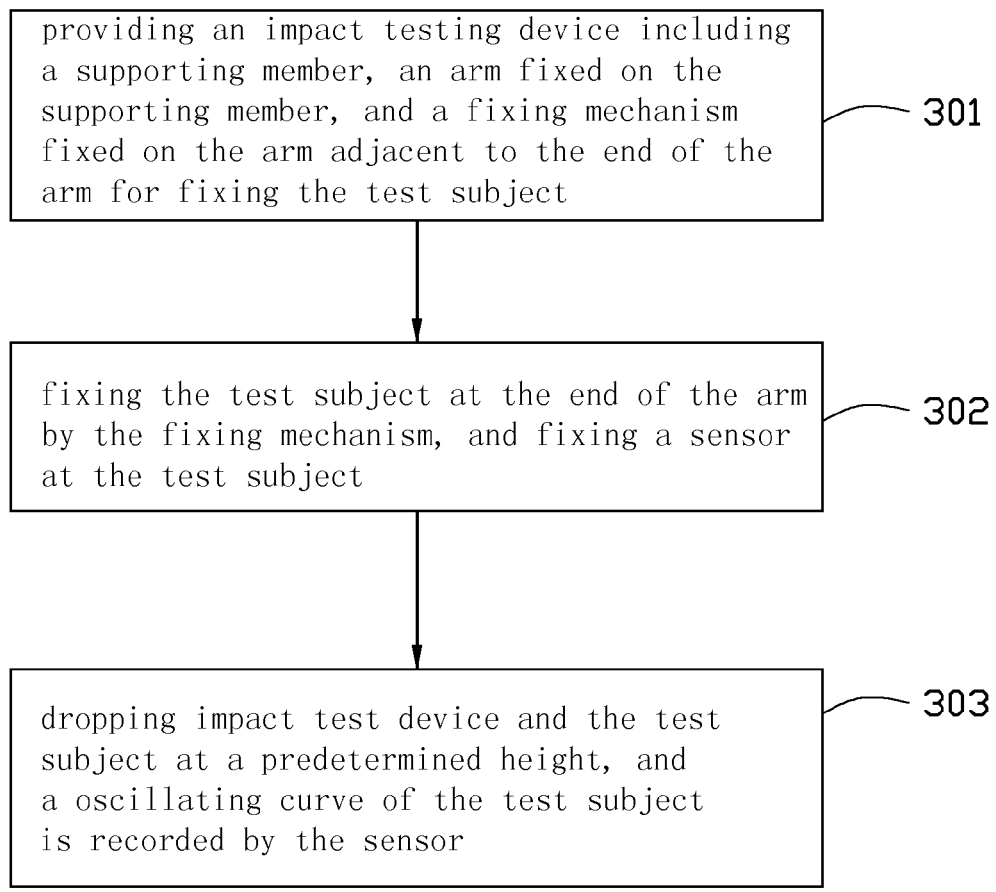
FIG. 3 is a flowchart of an impact testing method using the impact testing device shown in FIG. 2.

Referring to FIGS. 1 and 3, in step S301, an impact testing device 100 is provided as above;

In step S302, the test subject 200 is fixed on the free end 31 of the suspending arm 30 by the fixing mechanism 50, and a sensor 60 is provided and fixed on the test subject 200. The connecting member 203 of the test subject 200 is inserted between the holder 51 and the suspending arm 30. The threaded retainer 533 of the adjusting member 53 is threadedly engaged to securely fasten the connecting member 203 between the holder 51 and the suspending arm 30.

In step S303, the impact testing device 100 is dropped with the test subject 200 fixed on the impact testing device 100 from a predetermined height. The sensor 60 records an impact force applied on the test subject 200, and creates an oscillating curve according to the impact force detected.

Figure 4:
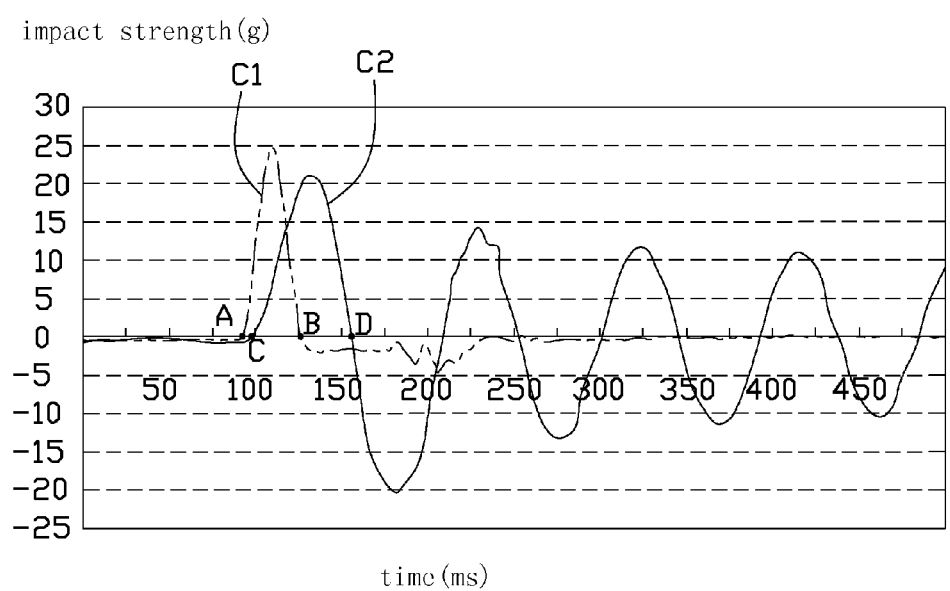
FIG. 4 is a graph showing an oscillating curve created in the impact method of FIG. 3.

FIG. 4 shows a broken oscillating curve C1 of the supporting member 10 when dropped from a predetermined height with an impact strength of 25 g (g is acceleration of gravity, 9.8 m/s²) lasting for 30.5 millisecond (ms) between time A and time B. Since the supporting member 10 is dropped on the ground before the test subject 200, a solid oscillating curve C2 of the test subject has lower amplitude and longer period than the broken oscillating curve C1. That is, the impact strength is reduced, and the impact duration is increased, thus, a more usable broken oscillating curve can be acquired for analysis. An oscillating curve between a time point C and D is considered as a main oscillating curve period. In the illustrated embodiment, the impact strength is 21.75 g, which is reduced by 13%, and the duration from the time point C to D is 54 ms, which is 77% increase. The time duration is adjustable by changing the particular receiving portion 33 through which the supporting member 10 passes through.

Finally, while particular embodiments have been described, the description is illustrative and is not to be construed as limiting. For example, various modifications can be made to the embodiments by those of ordinary skill in the art without departing from the true spirit and scope of the invention as defined by the appended claims.

What is claimed is:

1. An impact testing device for a test subject, comprising:
   a supporting member;
   a suspending arm with an end fixed on the supporting member, and the other end of the suspending arm being free; and
   a fixing mechanism fixed on the suspending arm adjacent to the free end of the suspending arm to fix the test subject, wherein the fixing mechanism comprises a holder to hold the test subject and one or more adjusting members to adjust a distance between the holder and the suspending arm, the adjusting member comprises a threaded rod and a threaded retainer corresponding to the threaded rod, the threaded rod passing through the holder and received and fastened in the threaded retainer, wherein a distance between the holder and the suspending arm is adjusted by moving the threaded retainer.

2. The impact testing device of claim 1, wherein the fixing mechanism comprises a fixing member fixed on the suspending arm, wherein an end of the threaded rod away from the adjusting member is fixed on the fixing member.

3. The impact testing device of claim 1, wherein the suspending arm defines a plurality of receiving portions whereby the supporting member is a threaded rod.

4. An impact testing device for a test subject comprising:
a supporting member;
a suspending arm with an end fixed on the supporting member, and the other end of the suspending arm comprising a free end; and
a fixing mechanism fixed on the suspending arm adjacent to the free end of the suspending arm to fix the test subject, wherein the fixing mechanism comprising a holder to hold the test subject and a plurality of adjusting members to adjust a distance between the holder and the suspending arm at each portion of the fixing mechanism on which each adjusting member is mounted individually.

5. The impact testing device of claim 4, wherein the adjusting member comprises a threaded rod and a threaded retainer corresponding to the threaded rod, the threaded rod passing through the holder and received and fastened in the threaded retainer, wherein a distance between the holder and the suspending arm is adjusted by moving the threaded retainer.

6. The impact testing device of claim 5, wherein the fixing mechanism comprises a fixing member fixed on the suspending arm, on which an end of the threaded rod away from the adjusting member is fixed.

7. The impact testing device of claim 5, wherein the suspending arm defines a plurality of receiving portions by which the supporting member is threadedly received selectively in one threaded hole.

8. An impact testing method for a test subject, the method comprising:
providing an impact test device comprising a supporting member, a suspending arm positioned on the supporting member and a fixing mechanism fixed at an end the suspending arm;
fixing the test subject at one end of the suspending arm by the fixing mechanism, and fixing a sensor on the test subject;
dropping the impact test device and the test subject together from a predetermined height, wherein an oscillating curve of the test subject is recorded by the sensor.

* * * * *